United States Patent
Reddy et al.

(10) Patent No.: US 6,773,631 B2
(45) Date of Patent: Aug. 10, 2004

(54) LIQUID OVERBASED MIXED METAL STABILIZER COMPOSITION OF CALCIUM, BARIUM AND ZINC FOR STABILIZING HALOGEN-CONTAINING POLYMERS

(75) Inventors: James E. Reddy, Lyndhurst, OH (US); Jeremy A. Hackett, Rocky River, OH (US)

(73) Assignee: Hammond Group, Inc., Hammond, IN (US)

( * ) Notice: Subject to any disclaimer, the term of this patent is extended or adjusted under 35 U.S.C. 154(b) by 312 days.

(21) Appl. No.: 10/097,724

(22) Filed: Mar. 15, 2002

(65) Prior Publication Data

US 2003/0104954 A1 Jun. 5, 2003

Related U.S. Application Data

(63) Continuation-in-part of application No. 09/861,393, filed on May 18, 2001, now Pat. No. 6,689,893.

(51) Int. Cl.$^7$ .......................... C09K 15/32; C09K 3/00; C07C 51/00
(52) U.S. Cl. .................. 252/400.52; 252/400.61; 252/407; 252/182.29; 554/156; 554/157
(58) Field of Search .............. 252/400.52, 400.61, 252/407, 182.29; 554/156, 157

(56) References Cited

U.S. PATENT DOCUMENTS

| | | | |
|---|---|---|---|
| 2,616,904 A | 11/1952 | Asseff et al. ............ 260/399 |
| 2,760,970 A | 8/1956 | Le Suer ............ 260/429 |
| 2,767,164 A | 10/1956 | Asseff et al. ............ 260/139 |
| 2,798,852 A | 7/1957 | Wiese et al. ............ 252/42.7 |
| 2,802,816 A | 8/1957 | Asseff et al. | |
| 3,027,325 A | 3/1962 | McMillen et al. ........ 252/33 |
| 3,031,284 A | 4/1962 | Andress, Jr. ............ 44/76 |
| 3,194,823 A | 7/1965 | Suer et al. ............ 260/414 |
| 3,342,733 A | 9/1967 | Robbins et al. ............ 252/33 |
| 3,533,975 A | 10/1970 | Scullin ............ 260/23 |
| 3,773,664 A | 11/1973 | Lesuer ............ 252/40.7 |
| 3,779,922 A | 12/1973 | LeSuer ............ 252/34.7 |
| 4,159,973 A | 7/1979 | Hoch et al. ............ 260/23 XA |
| 4,252,698 A | 2/1981 | Ito et al. ............ 260/18 EP |
| 4,501,840 A | * 2/1985 | Werle et al. ............ 524/387 |
| 4,661,544 A | * 4/1987 | Quinn ............ 524/109 |
| 4,665,117 A | * 5/1987 | Quinn ............ 524/327 |
| 4,743,397 A | * 5/1988 | Quinn ............ 252/400.61 |
| 5,322,872 A | 6/1994 | Quinn ............ 524/186 |
| 5,519,076 A | * 5/1996 | Odaira et al. ............ 524/112 |
| 5,746,961 A | 5/1998 | Stevenson et al. .......... 264/255 |
| 5,859,267 A | 1/1999 | Khattar et al. ............ 554/4 |
| 6,262,161 B1 | 7/2001 | Betso et al. ............ 524/425 |
| 6,689,893 B2 | * 2/2004 | Reddy et al. ............ 554/156 |

FOREIGN PATENT DOCUMENTS

| | | | | |
|---|---|---|---|---|
| DE | 198 60 798 A1 | 7/2000 | ............ C08L/27/02 |
| EP | 0 421 933 A1 | 4/1991 | ............ C08K/13/02 |
| RU | 2 087 491 C1 | 8/1997 | ............ C08L/27/08 |
| WO | WO 01/12708 A1 | 2/2001 | ............ C08K/3/00 |

* cited by examiner

*Primary Examiner*—Joseph D. Anthony
(74) *Attorney, Agent, or Firm*—Wood, Herron & Evans, L.L.P.

(57) ABSTRACT

Liquid overbased calcium/barium/zinc ternary systems are provided for stabilizing halogen-containing polymers. These overbased ternary stabilizer systems are shelf stable liquids and provide polyvinyl chloride compositions with improvements in thermal stability, early color, clarity and plate-out resistance.

21 Claims, No Drawings

LIQUID OVERBASED MIXED METAL STABILIZER COMPOSITION OF CALCIUM, BARIUM AND ZINC FOR STABILIZING HALOGEN-CONTAINING POLYMERS

RELATED APPLICATION

This application is a continuation-in-part application of application Ser. No. 09/861,393, filed May 18, 2001 now U.S. Pat. No. 6,689,893, directed to "Shelf Stable Haze Free Liquids of Overbased Alkaline Earth Metal Salts Processes and Stabilizing Halogen-Containing Polymers Therewith", which is incorporated herein by reference in its entirety.

FIELD OF THE INVENTION

The present invention relates to a liquid overbased mixed metal stabilizer composition of calcium, barium and zinc (Ca/Ba/Zn) for stabilizing halogen-containing polymers. Shelf stable haze free liquids of overbased calcium carboxylates are used to provide a mixed metal ternary stabilizer of calcium, barium and zinc. The liquid overbased ternary system of Ca/Ba/Zn provides polymers such as polyvinyl chloride (PVC) with improvements in thermal stability, early color, plate-out resistance and clarity.

BACKGROUND OF THE INVENTION

The preparation of overbased calcium or barium salts of carboxylic acids, alkyl phenols, and sulfonic acids are disclosed in the following U.S. Pat. Nos. 2,616,904; 2,760,970; 2,767,164; 2,798,852; 2,802,816; 3,027,325; 3,031,284; 3,342,733; 3,533,975; 3,773,664; and 3,779,922. The use of these overbased metal salts in the halogen-containing organic polymer is described in the following U.S. Pat. Nos. 4,159,973; 4,252,698; and 3,194,823. The use of overbased barium salt in stabilizer formulations has increased during recent years. This is due, in the main, to the fact that overbased barium salts possess performance advantages over the neutral barium salts. The performance advantages associated with overbased barium salts are low plate-out, excellent color hold, good long-term heat stability performance, good compatibility with the stabilizer components, etc. Unfortunately, most of the overbased barium salts are dark in color and, while these dark colored overbased barium salts are effective stabilizers for halogen-containing organic polymer, their dark color results in the discoloration of the end product. This feature essentially prohibits the use of dark colored overbased barium salts in applications where a light colored polymer product is desired.

According to the teachings of U.S. Pat. No. 4,665,117, light colored alkali or alkaline earth metal salts are prepared where alkyl phenol is used as a promoter. However, alkyl phenol is also a major cause for the development of color in the final product. This problem is overcome by the use of propylene oxide which displaces the hydrogen of the phenolic hydroxyl group and thereby restricts the formation of colored species. However, there are disadvantages associated with this approach, principally due to the toxic nature of propylene oxide. Propylene oxide is classified as a possible carcinogen and laboratory animal inhalation studies have shown evidence of a link to cancer. Propylene oxide is also listed as a severe eye irritant, and prolonged exposure to propylene oxide vapors may result in permanent damage to the eye. Furthermore, propylene oxide is extremely flammable and explosive in nature under certain conditions. Propylene oxide boils at 94° F. and flashes at −20° F. As a result, extreme precautions are required to handle propylene oxide at the plant site. Special storage equipment is required for propylene oxide and other safety features are necessary. U.S. Pat. No. 4,665,117 describes the use of propylene oxide at 150° C. At this temperature, propylene oxide will be in the gaseous phase. Under these operating conditions, more than stoichiometric amounts of propylene oxide are required to carry the reaction to completion because propylene oxide will escape from the reaction mixture and this requires additional handling of the excess propylene oxide.

With the movement in the plastics industry to remove heavy metals, liquid calcium-zinc stabilizers are desirous, but not practical, as replacements for barium-cadmium or barium-zinc. Low metal concentrations, poor compatibility, haziness in clear products and plate out during processing in PVC have severely limited the universal acceptance of calcium based liquid stabilizer compositions. Problems are encountered in the stability of these compositions upon standing or storage. Storage stability is due to the incompatibility among the metal salts employed in the composition and is exhibited by increased turbidity, viscosity, or insoluble solids over time. As a result, the liquid calcium compositions are no longer homogeneous or readily pourable and must be specially treated in order to be used. U.S. Pat. No. 5,322,872 is directed to stabilized compositions of mixed metal carboxylates having improved storage stability. According to this patent, a complexing agent is added to the mixed metal carboxylate in order to improve shelf stability. Complexing agents disclosed in this patent include phosphines, phosphites, aromatic cyanides, aromatic hydroxy compounds, oximes and other compounds. U.S. Pat. Nos. 5,830,935 and 5,859,267 have also issued as directed to processes for improving basic metal salts and stabilizing halogen-containing polymers therewith.

Notwithstanding the state of the art as exemplified by the above patents, there is a need for further improvements in making compositions of overbased alkaline earth metal carboxylates and in methods for their use in stabilizing halogen-containing polymers.

SUMMARY

The present invention relates to liquid overbased mixed metal stabilizer compositions of calcium, barium and zinc (Ca/Ba/Zn) for a halogen-containing polymer. The invention described in application Ser. No. 09/861,393, filed May 18, 2001, relates to a shelf stable haze free liquid of an overbased alkaline earth metal carboxylate. The shelf stable liquids that were described in that application have now been found to provide a mixed metal stabilizer composition with barium and zinc having improved properties in the stabilization of halogen-containing polymers.

A number of benefits are obtained by the liquid overbased Ca/Ba/Zn stabilizer products of this invention. In particular, shelf stabilities are achieved with the overbased Ca/Ba/Zn liquids with the reduction of phenol and phenolic derivatives such as phenolic reaction products. This is an especially desirable advantage in view of the efforts of the trade to reduce or eliminate such phenolic products because of environmental concerns. In addition, enhanced shelf stabilities for the liquid overbased calcium fatty acid carboxylates and barium/zinc mixed metal stabilizer compositions of this invention have been demonstrated over presently commercially available products. In particular, presently available liquid mixed metal systems exhibit the development of turbidity or haze, whereas the liquid compositions of this invention remain stable over extended periods of time. Therefore, the shelf stable and preferably haze free liquids of this invention allow easy handling, storage and filtration. Furthermore, when the liquid overbased Ca/Ba/Zn ternary stabilizer systems are employed in vinyl halide polymers, they exhibit better compatibilities with improvements in thermal stability, early color, clarity and plate-out resistance.

The Ca/Ba/Zn ternary stabilizer systems are employed in polyvinyl chloride (PVC) compositions in amounts of from about 1 to about 5 parts of stabilizer, preferably about 2–3 parts, per 100 parts PVC.

The metal ratio of Ca/Ba/Zn in such systems is on the order of about 3:14:2, within a general range of about 0.5% to 3% Ca, about 4% to 8% Ba, and about 0.5% to 3% Zn to achieve the benefits of this invention.

The above advantages, benefits and further understanding of this invention will be apparent with reference to the following detailed description and preferred embodiments.

DETAILED DESCRIPTION AND PREFERRED EMBODIMENTS

A. Shelf Stable Haze Free Liquids of Overbased Calcium Salts for Use In the Ca/Ba/Zn System In one preferred form of the invention, a shelf stable haze free liquid of a calcium salt of a fatty acid is used to make the Ca/Ba/Zn ternary system. The liquid comprises a calcium carbonate, a calcium carboxylate of a fatty acid, a liquid hydrocarbon, and an aliphatic alcohol having at least 8 carbon atoms, with the liquid being preferably free of a phenol or a phenolic derivative such as a phenolic reaction product.

In another form of the invention, the calcium sulfate, sulfide or sulfite may be formed instead of the carbonate where the acidic gas used in the process is sulfur dioxide, sulfur trioxide, carbon disulfide, or hydrogen sulfide.

The fatty acid of the overbased liquid calcium carboxylate is generally a $C_{12}$–$C_{22}$ fatty acid, including, for example, lauric, myristic, palmitic, stearic, archidic and behenic, among the saturated fatty acids. Unsaturated fatty acids include palmitoleic, oleic, linoleic, and linolenic. Among these fatty acids, oleic is presently preferred in preparing the overbased liquid carboxylates. For example, shelf stable haze free overbased calcium oleates have been prepared. These overbased calcium salts contain calcium carbonate, calcium oleate, a liquid hydrocarbon diluent and an aliphatic alcohol having at least 8 carbon atoms.

In a broad form of the invention, it is important to have an aliphatic alcohol having at least 8 carbon atoms, more preferably an alcohol having 8 to 14 carbon atoms, such as, isodecanol, dodecanol, octanol, tridecanol and tetradecanol. Isodecanol is presently preferred. It has been found that when a higher aliphatic alcohol is employed in making the overbased product, phenol may be excluded from the reaction as a promoter. This is a particularly advantageous feature of the invention where it is undesirable to have a phenol or phenolic reaction product involved in the manufacture or use of the overbased liquid.

In another form of the invention, the liquid overbased calcium salt of the fatty acid is believed to be a thermodynamically stable microemulsion. The microemulsion has micells and a continuous phase. The micells consist of an alkaline earth metal carbonate and an alkaline earth metal carboxylate of the fatty acid. The continuous phase of the microemulsion consists of the liquid hydrocarbon and the higher aliphatic alcohol.

Haze free liquids of the calcium and even barium may be employed in the Ca/Ba/Zn system. For instance, calcium or barium salts have been prepared containing at least 4% by weight or more of the alkaline earth metal up to about 36% by weight. In the case of the overbased calcium salts, up to about 13–15% by weight calcium are produced and, for barium salts, up to about 36% by weight barium may be produced. In the preparation of higher overbased products, for example, containing about 13–15% by weight metal, it has been found suitable to use a glycol or a glycol ether along with the higher aliphatic alcohol. A glycol or glycol ether may be selected from the group consisting of diethylene glycol monobutyl ether (butyl Carbitol®), triethylene glycol, dipropylene glycol, diethylene glycol monomethyl ether, ethylene glycol monobutyl ether, and mixtures thereof.

B. The Basic Process for Making the Overbased Calcium Salts and Critical Features The process for preparing a shelf stable haze free liquid of a calcium salt of a fatty acid comprises reacting an alkaline earth metal base and a fatty acid with an equivalent ratio of metal base to the fatty acid being greater than 1:1 in the presence of a mixture of liquid hydrocarbon. The basic process has been described in detail in application Ser. No. 09/861,393, filed May 18, 2001, of which this application is a continuation-in-part, which is incorporated in its entirety herein by reference. A surfactant and catalyst promote the reaction. The mixture is acidified and preferably carbonated to produce amorphous alkaline earth metal carbonate. During carbonation, a dispersion is added containing alkaline earth metal base, liquid hydrocarbon and an aliphatic alcohol having at least 8 carbon atoms in relative amounts at a controlled rate of base addition to produce a stable haze free liquid reaction product. Water is removed from the reaction product to produce a shelf stable haze free liquid overbased alkaline earth metal salt. Generally, it is preferred that the entire process be conducted in the absence of free oxygen and, for this purpose, an atmosphere of nitrogen is used.

One of the important features of the method is the step of adding during carbonation a dispersion of alkaline earth metal base, liquid hydrocarbon and an aliphatic alcohol having at least 8 carbon atoms at a controlled rate of base addition to produce the stable haze free liquid. It has been found that the addition of a dispersion of the base in the liquid hydrocarbon and aliphatic alcohol protects or passivates the base, thereby enabling the formation of a stable haze free liquid reaction product. By protecting or passivating the base, carbonation proceeds to produce amorphous alkaline earth metal carbonate. Unexpectedly, the reaction proceeds without the need to remove water during the reaction and results in a very stable haze free liquid reaction product. At the end of the reaction, water is removed, preferably to the level of less than 1%, more preferably less than 0.3% or 0.1%, in the obtainment of the shelf stable liquid overbased salt. The removal of water which is added during the reaction or formed by the reaction is necessitated because it forms a separate phase which impedes either the product of the reaction or the formation of a shelf stable haze free liquid.

Other features of the method include filtering the product of the reaction to produce a shelf or thermodynamically stable liquid at a product filtration rate of at least about 300 ml per 10 minutes. In a preferred form of the invention, the product which is produced is filterable to remove unwanted byproducts and enhance the shelf stability of the overbased liquid. For example, with a Buchner funnel having a 15 cm diameter under vacuum of about 25–30 inches Hg with a Whatman No. 1 filter and a diatomaceous filtering aid (Celite® 512–577), the product is filterable at satisfactory rates. One of the important discoveries of the method of this invention is the ability to filter the reaction product to form a stable haze free liquid at filtration rates which heretofore were unachievable. This was especially the case when higher levels of metal content in the overbased liquids were desired, especially overbased calcium liquids. Thus, filtration removes undesirable impurities including silica, iron oxide and other metal species, unreacted calcium hydroxide, calcium carbonate, and other oxides which may contribute to lack of stability. These byproducts or impurities may comprise up to about 6% of byproduct of the reaction.

Throughout this specification and claims, the term "basic" or "overbased" as applied to the alkaline earth metal salts is used to refer to metal compositions wherein the ratio of total metal contained therein to the fatty acid moieties is greater than the stoichiometric ratio of the neutral metal salt. That is, the number of metal equivalents is greater than the number of equivalents of the fatty acid. In some instances, the degree to which excess metal is found in the basic metal salt is described in terms of a "metal ratio". Metal ratio as used herein indicates the ratio of total alkaline earth metal in the oil-soluble composition to the number of equivalents of the fatty acid or organic moiety. The basic metal salts often have been referred to in the art as "overbased" or "superbased" to indicate the presence of an excess of the basic component.

The above process may be used to prepare shelf stable liquids of the calcium carboxylates of the fatty acids without the use of phenol promoter or phenolic reaction product. Therefore, liquid overbased barium fatty acid carboxylates may be made for use in the ternary system of Ca/Ba/Zn without the need for a phenol or phenolic reaction product in order to achieve a shelf stable haze free liquid. In the case of liquid overbased calcium fatty acid carboxylates, shelf stable haze free products are obtained without a phenol where the aliphatic alcohol having at least 8 carbon atoms is employed.

The alkaline earth metal bases utilized as a reaction component may be derived from any calcium bases. The metal bases include metal oxides and hydroxides and, in some instances, the sulfides, hydro sulfides, etc. While a phenolic component or reactant may preferably be excluded from a reaction, in the case of liquid overbased calcium products, the phenol or alkyl phenol may be included to yield liquid overbased products. As stated above, the fatty acids, or mixtures thereof, as identified above may be used in the reaction mixture. For example, a surfactant that facilitates the reaction is the alkaline earth metal carboxylate of the fatty acid that is formed in situ. Other surfactants may be included, for example, general purpose surface active agents identified under the trademark Tween which are polyoxyethylene derivatives of fatty acid partial esters of sorbitol anhydrides, particularly mono- and di-oleates of the ethoxylated sorbitol, and polyisobutylene succinic acid. Furthermore, it is desirable to include a catalyst to facilitate the speed of the reaction such as propionic acid, citric acid, acetic acid and adipic acid. The hydrocarbon liquid employed in the process and the liquid reaction products generally includes any hydrocarbon diluent. Most generally, the liquid hydrocarbon is selected from the group of an oil, mineral spirits and non-aromatic hydrocarbons.

C. Amounts of Reactants and Catalysts

The amount of alkaline earth metal base utilized in the preparation of basic salts is an amount which is more than one equivalent of the base per equivalent of fatty acid or organic moiety, and more generally, will be an amount sufficient to provide at least three equivalents of the metal base per equivalent of the acid. Larger amounts can be utilized to form more basic compounds, and the amount of metal base included may be any amount up to that amount which is no longer effective to increase the proportion of metal in the product. When preparing the mixture, the amount of fatty acid and the alcohol included in the mixture is not critical except that the ratio of equivalents of the metal base of the combination of the other components in the mixture should be greater than 1:1 in order to provide a basic product. More generally, the ratio of equivalents will be at least 3:1. In those instances where phenol may be present in making an overbased calcium, the ratio of equivalents of monocarboxylic acid to phenol should be at least about 1.1:1; that is, the monocarboxylic acid is present in excess with respect to the phenol.

The ranges of hydrocarbon oil, aliphatic alcohol (preferably isodecanol), butyl Carbitol and triethylene glycol have been selected such that, in the presence of the alkaline earth fatty acid salt (i.e., Ca oleate) which acts as a primary surfactant, the mixture forms a stable inverse microemulsion of the metal carbonate, water, and surfactant (internal phase) and surfactant, cosurfactant, and hydrocarbon (external continuous phase).

The acceptable ratios of hydrocarbon oil to cosurfactant aliphatic alcohol (isodecanol) are about 2:1 to about 4:1, with about 2:1 preferred. The glycol ethers may be used at about 1–15% of the final product, butyl Carbitol preferably at about 6%, and triethylene glycol at about 0–2%, preferably at about 0.6%.

The lime slurry which is added to the oleic acid in the reaction is formulated to be an easily pumpable mixture with the general composition of about 40–50% lime, about 25–40% hydrocarbon oil, about 10–25% isodecanol, and about 0–10% butyl Carbitol. The butyl Carbitol amount that is needed to make a pumpable slurry increases as the % lime in the slurry increases.

The reaction mixture for an overbased calcium oleate, after addition of the slurry and carbonation with carbon dioxide, preferably has the following composition ranges:

| | |
|---|---|
| Ca oleate (surfactant) | about 15–30% |
| Ca carbonate | about 9–35% |
| Hydrocarbon oil | about 30–35% |
| Isodecanol (cosurfactant) | about 15–18% |
| Butyl Carbitol | about 4–6% |
| Triethylene glycol | about 0–0.8% |

The catalyst, propionic acid or a lower aliphatic mono, di, or tricarboxylic acid is used in the amount of about 0–0.1% of the final reaction mixture.

The step of carbonation involves treating the mixtures described above with an acidic gas in the absence of free oxygen until the titratable basicity is determined using phenolphthalein. Generally, the titratable basicity is reduced to a base number below about 10. The mixing and carbonation steps of the present invention require no unusual operating conditions other than preferably the exclusion of free oxygen. The base, fatty acid and liquid hydrocarbon are mixed, generally heated, and then treated with carbon dioxide as the acidic gas, and the mixture may be heated to a temperature which is sufficient to drive off some of the water contained in the mixture. The treatment of the mixture with the carbon dioxide preferably is conducted at elevated temperatures, and the range of temperatures used for this step may be any temperature above ambient temperature up to about 200° C., and more preferably from a temperature of about 75° C. to about 200° C. Higher temperatures may be used such as 250° C., but there is no apparent advantage in the use of such higher temperatures. Ordinarily, a temperature of about 80° C. to 150° C. is satisfactory.

By the term "acidic gas" as used in this specification and in the claims is meant a gas which upon reaction with water will produce an acid. Thus, such gases as sulfur dioxide, sulfur trioxide, carbon dioxide, carbon disulfide, hydrogen sulfide, etc., are exemplary of the acidic gases which are useful in the process of this invention. Of these acids, sulfur dioxide and carbon dioxide are preferred, and the most preferred is carbon dioxide. When carbon dioxide is used the alkaline earth carbonate is formed. When the sulfur gases are used, the sulfate, sulfide and sulfite salts are formed.

D. Halogen-Containing Polymer

A halogen-containing polymer, such as a vinyl halide resin, most commonly stabilized with the basic metal salts of this invention is polyvinyl chloride. It is to be understood, however, that this invention is not limited to a particular vinyl halide resin such as polyvinyl chloride or its copolymers. Other halogen-containing resins which are employed and which illustrate the principles of this invention include chlorinated polyethylene, chlorosulfonated polyethylene, chlorinated polyvinyl chloride, and other vinyl halide resin types. Vinyl halide resin, as understood herein, and as appreciated in the art, is a common term and is adopted to define those resins or polymers usually derived by polymerization or copolymerization of vinyl monomers including vinyl chloride with or without other comonomers such as ethylene, propylene, vinyl acetate, vinyl ethers, vinylidene chloride, methacrylate, acrylates, styrene, etc. A simple case is the conversion of vinyl chloride $H_2C=CHCl$ to polyvinyl chloride $(CH_2CHCl-)_n$ wherein the halogen is bonded to the carbon atoms of the carbon chain of the polymer. Other examples of such vinyl halide resins would include vinylidene chloride polymers, vinyl chloride-vinyl ester copolymers, vinyl chloride-vinyl ether copolymers, vinyl chloride-vinylidene copolymers, vinyl chloride-propylene copolymers, chlorinated polyethylene, and the like. Of course, the vinyl halide commonly used in the industry is the chloride, although others such as bromide and fluoride may be used. Examples of the latter polymers include polyvinyl bromide, polyvinyl fluoride, and copolymers thereof.

The barium and zinc compound stabilizers which may be used with the overbased calcium salt in the ternary Ca/Ba/Zn system are well known. These metal compounds serve to capture HCl liberated during heat processing of the vinyl halide resin composition into its final shape. The barium or zinc compound stabilizers are usually metal salts of a carboxylic acid, advantageously of a $C_8$–$C_{24}$ carbon chain link monocarboxylic acid such as lauric, oleic, stearic, octoic, or similar fatty acid salts. Metal salts of alkyl phenates may be used. Mixed metal salts of carboxylic acids, and their preparation, are familiar to those skilled in the art to which this present invention pertains. Mixed metallic carboxylates involving barium/zinc blends alone and in combination with other stabilizers or additives such as beta-diketones, phosphite salts and phenolic antioxidants may be used.

E. End Uses for the Stabilizers

The overbased liquid stabilizers Ca/Ba/Zn of this invention may be used in a number of end products. Examples include:
wall covering, flooring (vinyl tile and inlay), medical devices, dip coating, chair mat, banner film, pigment dispersion, vinyl siding, piping, fuel additive, cosmetic, ceiling tile, roofing film, wear layer, play balls or toys, teethers, fencing, corrugated wall panels, dashboards, and shifter boots.

The following Examples illustrate the preparation of the shelf stable haze free liquids of the overbased calcium salts in accordance with the method of the present invention and the liquid overbased Ca/Ba/Zn stabilizers prepared therefrom. However, these examples are not considered to be limiting the scope of this invention. Unless otherwise indicated in the following examples and elsewhere in the specification and claims, all parts and percentages are by weight, and all temperatures are in degrees Fahrenheit.

EXAMPLE 1

10% Overbased Calcium Oleate/Carbonate

A phenol-free 10% overbased calcium oleate/carbonate was prepared according to this Example. A mixture of 308.42 g of oleic acid (1.100 moles), 213.15 g mineral oil, 154.14 g of isodecyl alcohol, 63.08 g of butyl Carbitol, 8.70 g of triethylene glycol, 26.97 g of water and 0.87 g of propionic acid was heated to 190° F., with stirring, under a nitrogen atmosphere. To the stirred mixture there was continuously added a dispersion comprised of 38.98 g mineral oil, 13.86 g isodecyl alcohol, 3.71 g butyl Carbitol and 43.28 g of lime (0.5498 moles) for about 33 minutes to produce a solution of calcium oleate in the mixture. The dispersion was added at a rate of about 3 g per minute. At this point in the reaction, the mixture tested basic with phenolphthalein (about 10–12 pH). Then, to the stirred mixture there was continuously added, over a period of about 3 hours and 56 minutes, a dispersion comprised of 276.25 g mineral oil, 98.23 g isodecyl alcohol, 26.31 g butyl Carbitol and 306.75 g lime (3.897 moles) while the mixture was being treated with carbon dioxide at 1.5 SCFH at 195–200° F. The dispersion was also added at a rate of about 3 g per minute. The basicity of the reaction was checked to maintain the basicity during the reaction. When the reaction mixture tested nearly neutral to phenolphthalein, the carbon dioxide addition was discontinued. The reaction mixture was then heated to 300° F. and a total of 99.36 g of water was removed via a Dean-Stark trap. The resulting product mixture was stirred and 24.00 g of filter aid (diatomaceous earth) was added. The product mixture was filtered with suction, as stated above in the description, at about 300 ml per 10 minutes, yielding a clear, amber, mobile liquid filtrate of overbased calcium oleate/carbonate which remained clear upon cooling to room temperature. The filtrate was analyzed to contain 10.4% calcium by weight.

EXAMPLE 2

14% Overbased Calcium Oleate/Carbonate

A phenol-free overbased calcium oleate/carbonate containing 14% calcium by weight was made according to this Example. In a 3-liter resin kettle equipped with an overhead stirrer, two gas inlet tubes, a thermocouple, heating mantle and Dean-Stark trap with condenser, was added 1700 g of a 9.89% overbased calcium oleate/carboxylate made by the method of the previous example and 42.5 g of deionized water. The mixture was heated with stirring under a nitrogen atmosphere to a temperature of 195° F., and a slurry containing 385 g of hydrated lime (94% calcium hydroxide), 231 g of hydrocarbon oil, 96.25 g of isodecyl alcohol, and 57.75 g of butyl Carbitol was added at a rate of 3.42 g per minute over a 3 hour 45 minute period. After 5 minutes of slurry addition, carbon dioxide was added to the reaction at a rate of 1.2 standard cubic feet per hour. During the carbonation, a temperature of 195–200° F. was maintained and pH was monitored as in Example 1.

After the slurry addition was finished, the carbon dioxide addition was continued until the reaction mixture was neutral, as shown by a colorless sample when tested with phenolphthalein. The reaction mixture was then heated to 300° F. and both the water added and the water produced in the reaction was removed via the Dean-Stark trap. To the dehydrated reaction product was added 75 g of diatomaceous earth and the product was filtered with suction, as above in Example 1, yielding a clear, amber, mobile liquid filtrate of overbased calcium oleate/carboxylate which remained clear on cooling to room temperature. The filtrate was analyzed to contain 14.5% calcium by weight.

Shelf Stable Haze Free Liquid Tests
Shelf Stability of the Phenol-Free Liquid Overbased Calcium Carboxylate/Carbonate of Example 1

Shelf stability of the phenol-free liquid overbased calcium carboxylate/carbonate of Example 1 (referred to hereinafter as New Calcium) was measured using a turbidity meter over a period of 60 days in order to study its shelf stability properties. The Old Calcium referred to hereinafter is a formerly commercially available overbased calcium carboxylate containing 14% Ca (Lubrizol's product LZ 2118, OMG Plastistab 2118).

The following Table I summarizes the results:

TABLE I

|  | 1 Day | 7 Days | 10 Days | 22 Days | 60 Days |
|---|---|---|---|---|---|
| Stabilizer containing New Calcium | 7.8 | 7.7 | 8.0 | 7.7 | 7.5 |
| Stabilizer containing Old Calcium | >200 | >200 | >200 | >200 | >200 |

Turbidity readings were measured in Jackson Turbidity Units (JTU). The turbidity observation between 1–30 indicates that the product is free from haze, and the observation above 30 to 200 JTU indicates that the product is hazy in nature. If the turbidity observation stays constant over a period of time, this means that the product possesses good shelf stability. This means that the product does not pick up any haze or undergo change in physical appearance over a period of time.

The data of Table I shows that the New Calcium possessed good shelf stability over a 60-day period, whereas the commercially available Old Calcium is hazy in nature.

Shelf Stability of Mixed Metal Stabilizer of Phenol-Free Overbased Calcium Carboxylate/Carbonate and Zinc Carboxylate (Calcium/Zinc Stabilizer)

Shelf stability of mixed metal calcium/zinc stabilizers containing New Calcium (Example 1) and Old Calcium was also monitored over a period of 24 days as shown in Table II. The stabilizer formulation contained 5% Ca, 1.2% Zn (zinc octoate), 3.5% P (diphenyl isodecyl phosphite), 5% carboxylic acid (oleic acid), 3% anti-oxidant, 3% β-diketone (dibenzoyl methane) and diluent.

TABLE II

|  | 1 Day | 4 Days | 7 Days | 10 Days | 24 Days |
|---|---|---|---|---|---|
| Stabilizer containing New Calcium | 23.2 | 25.1 | 26.2 | 24.4 | 24.7 |
| Stabilizer containing Old Calcium | >200 | >200 | >200 | >200 | >200 |

The data illustrates that incorporation of New Calcium, versus Old Calcium, makes the mixed metal stabilizer shelf stable and haze free.

The above shelf stability tests were repeated by incorporating the New Calcium into a second stabilizer formulation. Shelf stability and clarity of a calcium/zinc stabilizer containing New and Old Calcium was monitored over a 24-day period, and the results are shown in Table III. Stabilizer formulation contained 5% Ca, 1.2% Zn (zinc octoate), 3.4% P (diphenyl decyl phosphite) 6% carboxylic acid (3% oleic acid/3% benzoic acid), 3% nonyl phenol as an anti-oxidant, 2% β-diketone (octyl benzoyl methane) and diluent.

TABLE III

|  | 1 Day | 4 Days | 7 Days | 10 Days | 24 Days |
|---|---|---|---|---|---|
| Stabilizer containing New Calcium | 25.1 | 26.3 | 28.1 | 26.5 | 26.8 |
| Stabilizer containing Old Calcium | >200 | >200 | >200 | >200 | >200 |

Again, the data illustrates that the New Calcium produces a shelf stable haze free mixed metal stabilizer versus the Old Calcium.

Shelf Stability of Mixed Metal Stabilizer of Overbased Calcium/Tin Carboxylate Stabilizers (Calcium/Tin Stabilizer)

Shelf stability of a calcium/tin stabilizer containing New Calcium (Example 1) and Old Calcium was monitored over a period of 25 days as shown in Table IV. Stabilizer formulation contained 5% Ca, 1.5% Sn (tin maleate), 3% P (diphenyl decyl phosphite), 5% carboxylic acid (oleic acid), 2% anti-oxidant (bisphenol-A), 3% β-diketone (dibenzoyl methane) and diluent.

TABLE IV

|  | 1 Day | 4 Days | 7 Days | 11 Days | 25 Days |
|---|---|---|---|---|---|
| Stabilizer containing New Calcium | 52 | 54 | 58 | 61 | 62 |
| Stabilizer containing Old Calcium | >200 | >200 | >200 | >200 | >200 |

The data illustrates that the incorporation of New Calcium, versus Old Calcium, makes the stabilizer shelf stable.

Performance Comparisons: Thermal Degradation of PVC

The New Calcium (Example 1) and Old Calcium were incorporated into mixed metal stabilizer compositions for the purpose of observing their relative rate of thermal degradation in PVC. The stabilizer compositions are as follows:

| Stabilizer formulation | A | B |
|---|---|---|
| New Calcium | 5.5% Ca | — |
| Old Calcium (2118) | — | 5.5% Ca |
| Zinc carboxylate | 1.2% Zn | 1.2% Zn |
| Organic Phosphite | 3.0% P | 3.0% P |
| Carboxylic Acid | 4.0% | 4.0% |
| Anti-oxidant | 3.0% | 3.0% |
| Beta Diketone | 3.0% | 3.0% |
| Diluent | as needed | as needed |

The performances of these stabilizers A and B were observed in a PVC formulation containing 100 parts of PVC resin (K value 66), 30 parts phthalate plasticizer, 3 parts of epoxidized soybean oil and 2 parts of either stabilizer A or B.

Stabilized PVC compounds were then milled at 350–360° F. for 5 minutes at 25 mil thickness. The thermal stability was carried out at 375° F. over 56 minutes. Yellowness [+b chromaticity of CIELAB color space (Commission Internationale de l'Eclairage) developed in 1976] was measured with a Minolta calorimeter. The yellowness values of the rate of thermal degradation are shown in the following Table V.

The PVC formulation containing the stabilizer with the New Calcium (A) develops color at a slower rate than the PVC formulation using the stabilizer with the Old Calcium (B).

TABLE V

| Time (minutes) | New Calcium A | Old Calcium B |
|---|---|---|
| 7 | 9.68 | 10.11 |
| 14 | 10.52 | 10.68 |
| 21 | 11.76 | 11.54 |
| 28 | 15.25 | 14.89 |
| 35 | 18.39 | 19.59 |
| 42 | 38.57 | 47.77 |
| 49 | 46.69 | 56.92 |
| 56 | 60.11 | 69.33 |

Performance Comparisons: Clarity

The New Calcium (Example 1) and Old Calcium, along with a calcium carboxylate ($C_8$), were incorporated into mixed metal stabilizer compositions for the purpose of observing their influence on the clarity of the PVC application. The stabilizer compositions are as follows:

| Stabilizer Formulation | A | B | C |
|---|---|---|---|
| New Calcium | 5.5% | — | — |
| Old Calcium | — | 5.5% | — |
| Calcium Carboxylate ($C_8$) | — | — | 5.5% Ca |
| Zinc carboxylate | 1.2% Zn | 1.2% Zn | 1.2% Zn |
| Organic Phosphite | 3.4% P | 3.4% P | 3.4% P |
| Carboxylic Acid | 5.0% | 5.0% | 5.0% |
| Anti-oxidant | 3.0% | 3.0% | 3.0% |
| Beta Diketone | 2.0% | 2.0% | 2.0% |
| Diluent | as needed | as needed | as needed |

The relative degree of clarity of the 0.25 inch pressed PVC formulations containing either stabilizer A, B or C was observed after 5 minutes of exposure to 350° F. and 15,000 pounds pressure. The PVC formulation comprised of 100 parts PVC resin (K value 66), 30 parts phthalate plasticizer, 3 parts of epoxidized soybean oil and 2 parts of either stabilizer A, B or C.

The pressed PVC samples were placed vertically near printed material to determine the crispness of the print when looking through the press. Stabilizer A and B gave comparable crispness. However, both stabilizer A and B gave better clarity or crispness than stabilizer C.

Performance Comparisons: Plate Out

The New Calcium (Example 1) and Old Calcium along with a non-carbonated calcium carboxylate were incorporated into mixed metal stabilizer compositions for the purpose of observing their influence on the resistance to plate out of the stabilizer during processing of the vinyl formulation. The stabilizer compositions have been identified above as A, B and C with A containing the New Calcium, B containing the Old Calcium and C containing the non-carbonated calcium carboxylate.

Plate out is determined by introducing a red pigment into a PVC formulation containing the stabilizer and allowing the pigment to migrate from the formulation to the metal rolls of a two roll mill at 340° F. A white clean up compound is then placed onto the rolls and the degree of plate out is determined by the amount of red picked up by the clean up compound. The colorimeter assigns a numerical value on the CIELAB scale for the degree of redness or plate out (+a).

| Red pigmented formulation: | | Clean up compound | |
|---|---|---|---|
| 100 | PVC resin | 100 | PVC resin |
| 40 | phthalate plasticizer | 40 | phthalate plasticizer |
| 8 | epoxidized soybean oil | 8 | epoxidized soybean oil |
| 0.2 | stearic acid | 0.2 | stearic acid |
| 2 | red 2B pigment | 4 | Titanium dioxide |
| 1.5 | stabilizer | 3 | lead phosphite |

The red formulation is milled for 4 minutes undisturbed after which the clean up compound is introduced and milled for three minutes undisturbed.

Colorimeter readings, +a value indicating increasing degree of red:

| Sample | a-value |
|---|---|
| A | −2.28 |
| B | −2.07 |
| C | +24.3 |

There is essentially no difference between the New and Old Calcium as far as plate out resistance. However, there is a significant difference between A and C where the New Calcium provides superior plate out resistance.

Liquid Overbased Ca/Ba/Zn System for Comparison with Neutral Liquid and Solid Trimetal Stabilizers Stabilizer formulations of overbased, neutral and solid trimetal components were formulated as reported in Table VI.

TABLE VI

| Components | Overbased | Neutral | Solid |
|---|---|---|---|
| Solid Ba Stearate (21% Ba) | | | 40% |
| Solid Ca Stearate (7.5% Ca) | | | 40% |
| Solid Zn Stearate (10% Zn) | | | 20% |
| Overbased 34.5% Ba | 14.5% | | |
| Overbased 10.2% Ca | 10.0% | | |
| Overbased 22.5% Zn | 3.1% | | |
| Neutral 19% Ba | | 26.0% | |
| Neutral 5% Ca | | 20.0% | |
| Neutral 15.5% Zn | | 4.4% | |
| DPDP (Phosphite) | 30.0% | 30.0% | |
| DPP (Phosphite) | 3.0% | 3.0% | |
| Oleic Acid | 3.0% | 3.0% | |
| Benzoic Acid | 3.0% | 3.0% | |
| Antioxidant | 3.0% | 3.0% | |
| Beta Diketone | 3.0% | 3.0% | |
| Diluent | 27.4% | 4.6% | |

The stabilizers of Table VI were formulated as typical representations of a sold, neutral and overbased heat stabilizer. A typical solid heat stabilizer is a blend of metal stearates. The liquid stabilizers, which can be either neutral or overbased, typically contain phosphites, antioxidants, etc.

A typical trimetal composition was made by blending Ca, Ba and Zn stearates by hand to provide a metal content of 3%, 8.4% and 2%, respectively. An overbased liquid composition of this invention was formulated by blending a haze free overbased calcium oleate/carbonate liquid made as in Example 1 with a barium oleate/carbonate similarly made and a zinc octoate (2-ethylhexoate) in the amounts shown at a metal content of Ba/Ca/Zn at 5%, 1%, 0.7%, respectively.

The neutral composition of Ba, Ca and Zn at the same metal content levels of the overbased stabilizer was formulated from barium neodecanoate, calcium neodecanoate and zinc octoate.

The above trimetal stabilizer formulations of Table VI at 2.5 parts were tested in a generic clear PVC compound consisting of 100 parts PVC resin (Oxy 240), 35 parts dioctylphthalate, 2.5 parts epoxidized soy bean oil, and stabilizer.

Experimental

Shelf Stability: The liquid overbased and neutral trimetal stabilizers display no visual precipitation. Turbidity readings in JTU units were taken over a period of 120 days as reported in Table VII.

TABLE VII

|          | 1 day | 30 days | 60 days | 120 days |
|----------|-------|---------|---------|----------|
| Overbased | 2.2   | 2.1     | 2.1     | 2.1      |
| Neutral  | 3.0   | 2.9     | 2.9     | 2.9      |

Thermal Stability: The trimetal stabilizers of Table VI were each incorporated into the PVC compound and milled at 350° F. They were fused for 5 minutes and then sheeted off of the two-roll mill. The thermal stability was carried out in a forced air oven at 375° F. for 90 minutes. The yellowness value (CIELAB) was measured as a rate of thermal degradation. The b-Values (yellowness) are listed in the following Table VIII.

TABLE VIII

| Time | Overbased | Neutral | Solid |
|------|-----------|---------|-------|
| 0    | 7.67      | 8.27    | 8.59  |
| 10   | 8.15      | 8.69    | 18.8  |
| 20   | 8.9       | 10.99   | 25.02 |
| 30   | 12.7      | 10.94   | 34.37 |
| 40   | 20.81     | 15.08   | 36.37 |
| 50   | 22.05     | 18.2    |       |
| 60   | 40.04     | 40.36   |       |
| 75   | 59.4      | 60.21   |       |

Dynamic Mill Stability: Again, each of the three trimetal stabilizers of Table VI were incorporated into the PVC compound and then placed on the two-roll mill at 350° F. until either burning, adhering, or until the color was determined to be too dark (b-value over 20). Yellowness values were taken on the milled material to measure the rate of degradation. The values are listed in the following Table IX.

TABLE IX

| Time | Overbased | Neutral | Solid |
|------|-----------|---------|-------|
| 1    | 8.01      | 8.67    | 12.98 |
| 10   | 8.05      | 8.64    | 14.88 |
| 20   | 8.43      | 9.87    | 14.84 |
| 30   | 8.72      | 10.41   | 21.32 |
| 40   | 9.49      | 11.15   |       |
| 50   | 10.03     |         |       |

Dynamic Brabender Stability: The three trimetal stabilizers of Table VI were each incorporated into the PVC compound. They were then tested under high temperature and high shear conditions using a Brabender mixer head #5 at 90° C. with a mixing speed of 60 rpm. Samples were pulled every 3 minutes for 27 minutes of the test. Yellowness values were taken on the samples to measure the rate of degradation as shown on the following Table X.

TABLE X

| Time | Overbased | Neutral | Solid |
|------|-----------|---------|-------|
| 3    | 10.76     | 14.36   | 22.9  |
| 6    | 11.17     | 13.9    | 26.25 |
| 9    | 13.15     | 14.76   | 31.46 |
| 12   | 13.8      | 15.49   | 41.17 |
| 15   | 17.06     | 17.03   | 39.95 |
| 18   | 24.17     | 18.69   | 46.15 |
| 21   | 24.17     | 18.69   | 46.15 |
| 24   | 38.64     | 28.66   | 44.79 |
| 27   | 44.67     | 37.48   | 42.91 |

Plate-Out: The plate-out procedure outlined above for the haze free overbased calcium metal salts was followed for evaluation of each trimetal stabilizer. Using a red pigment to deposit on the rolls of the two-mill, a clean up compound was used to pick up the deposited pigment. The a-value (redness) was measured to determine the amount of plate-out. The larger the a-value, the worse the plate out, as shown in Table XI.

TABLE XI

|         | Overbased | Neutral | Solid |
|---------|-----------|---------|-------|
| a-value | −1.15     | 12.15   | 8.31  |

Clarity: A press plate of each milled trimetal stabilizer was made to determine each stabilizer's effect on the clarity of the PVC compound. The stabilizer prepared using the overbased Ca/Ba/Zn offers the best clarity and color based on visual inspection. The procedure followed for this test is outlined above for the haze free liquid overbased calcium metal salts.

The above experimental data demonstrates the far superior early color properties of the overbased liquid Ca/Ba/Zn stabilizer system upon comparison with the neutral and solid trimetal systems. This is particularly shown in Table X by the dynamic Brabender stability tests over the time frame of 3 to 12 minutes. Significant improvements in dynamic mill stability of the overbased liquid Ca/Ba/Zn stabilizer system were also shown in Table IX over the neutral and solid trimetal systems. Improved plate-out resistance of the overbased liquid Ca/Ba/Zn system was also dramatically demonstrated in Table XI over the neutral and solid trimetal systems. The best clarity was also observed for the inventive overbased liquid Ca/Ba/Zn stabilizer system. All of these beneficial properties were achieved with the shelf stable liquid overbased Ca/Ba/Zn systems of this invention as shown by Table VII with maintenance of thermal stability as shown by Table VII.

The above description provides a disclosure of particular embodiments of the invention and is not intended for the purpose of limiting the same thereto. As such, the invention is not limited to only the above described embodiments, rather, it is recognized that one skilled in the art would understand alternative embodiments in view of the above description that fall within the scope of the invention.

What is claimed is:

1. A liquid overbased Ca/Ba/Zn trimetal stabilizer composition for a halogen-containing polymer comprising a mixture of a barium compound stabilizer and a zinc compound stabilizer, and a shelf stable haze free liquid of an overbased calcium salt of a fatty acid comprising, (a) a calcium salt of carbonate,
(b) a calcium carboxylate of a fatty acid,
(c) a liquid hydrocarbon, and
(d) an aliphatic alcohol having at least 8 carbon atoms, said liquid being essentially free of a phenol or phenolic derivative;
wherein said shelf stable haze free liquid of an overbased calcium salt of a fatty acid is prepared by a process comprising,
reacting a calcium base and a fatty acid with an equivalent ratio of calcium base to fatty acid being greater than 1:1 in the presence of liquid hydrocarbon, carbonating the mixture to produce amorphous calcium carbonate,
adding during carbonation a dispersion of calcium base, a liquid hydrocarbon and an aliphatic alcohol having at least 8 carbon atoms in relative amounts at a controlled rate of calcium base to produce a stable haze free liquid reaction product, and removing water from the reaction product to obtain a shelf stable haze free liquid overbased product containing calcium carboxylate of a fatty acid and a calcium carbonate;
said mixture of barium and zinc compound stabilizers and liquid overbased calcium carboxylate are in relative amounts to provide said liquid overbased Ca/Ba/Zn trimetal stabilizer for stabilizing a halogen-containing polymer.

2. The liquid overbased stabilizer composition of claim 1 wherein the liquid overbased calcium salt is calcium oleate/carbonate.

3. The liquid overbased stabilizer composition of claim 1 wherein the liquid hydrocarbon is selected from the group consisting of an oil, mineral spirits and non-aromatic hydrocarbons.

4. The liquid overbased stabilizer composition of claim 1 wherein the amount of metal in the Ca/Ba/Zn trimetal stabilizer is about 0.5% to 3% Ca, about 4% to 8% Ba, and about 0.5% to 3% Zn.

5. The liquid overbased stabilizer composition of claim 1 wherein the liquid overbased calcium salt is a salt of a $C_{12}$–$C_{22}$ fatty acid.

6. The liquid overbased stabilizer composition of claim 5 wherein said fatty acid is oleic acid.

7. The liquid overbased stabilizer composition of claim 1 wherein the alcohol has 8 to 14 carbon atoms.

8. The liquid overbased stabilizer composition of claim 7 wherein said alcohol is selected from the group consisting of isodecanol, dodecanol, octanol, tridecanol and tetradecanol, and mixtures thereof.

9. The liquid overbased stabilizer composition of claim 8 which further contains a glycol or a glycol ether.

10. The liquid overbased stabilizer composition of claim 9 wherein the glycol or glycol ether is selected from the group consisting of diethylene glycol monobutyl ether, triethylene glycol, dipropylene glycol, diethylene glycol monomethyl ether, ethylene glycol monobutyl ether, and mixtures thereof.

11. The liquid overbased stabilizer composition of claim 1 containing about 4% up to about 36% by total weight of the barium and calcium metals.

12. The liquid overbased stabilizer composition of claim 11 wherein calcium is contained in an amount of about 9% to about 15% by weight.

13. The liquid overbased stabilizer composition of claim 1 wherein the barium compound is a barium carboxylate of a fatty acid.

14. The liquid overbased stabilizer composition of claim 13 wherein the barium carboxylate is an overbased barium carboxylate.

15. The liquid overbased stabilizer composition of claim 14 wherein said overbased barium carboxylate is barium oleate/carbonate.

16. The liquid overbased stabilizer composition of claim 1 wherein said zinc compound is a zinc carboxylate.

17. The liquid overbased stabilizer composition of claim 16 wherein said zinc carboxylate is formed from a $C_8$–$C_{24}$ carboxylic acid.

18. The liquid overbased stabilizer composition of claim 17 wherein said acid is selected from the group consisting of 2-ethyl hexanoic acid and neodecanoic acid, and mixtures thereof.

19. A shelf stable liquid overbased Ca/Ba/Zn trimetal stabilizer composition comprising
(a) a shelf stable haze free liquid of overbased calcium oleate and calcium carbonate, a hydrocarbon liquid and an alcohol having at least 8 carbon atoms, wherein said shelf stable haze free liquid of an overbased calcium oleate is prepared by a process comprising, <reacting a calcium base and oleic acid with an equivalent ratio of calcium base to oleic acid being greater than 1:1 in the presence of liquid hydrocarbon, carbonating the mixture to produce amorphous calcium carbonate,
adding during carbonation a dispersion of calcium base, a liquid hydrocarbon and an aliphatic alcohol having at least 8 carbon atoms in relative amounts at a controlled rate of calcium base to produce a stable haze free liquid reaction product, and removing water from the reaction product to obtain a shelf stable haze free liquid overbased product containing calcium oleate and calcium carbonate; and
(b) a mixture of barium and zinc metal compound stabilizers,
said components of said liquid overbased Ca/Ba/Zn trimetal stabilizer are contained in relative amounts for stabilizing a polyvinyl chloride polymer or copolymer.

20. The liquid overbased composition of claim 19 wherein the barium compound is a barium carboxylate of a fatty acid and the zinc compound is a zinc carboxylate having $C_8$–$C_{24}$ carbon atoms.

21. The liquid overbased stabilizer composition of claim 19 wherein the barium compound is an overbased barium oleate/carbonate and the zinc compound is selected from the group consisting of zinc octoate and zinc neodecanoate, and mixtures thereof.

* * * * *

UNITED STATES PATENT AND TRADEMARK OFFICE
CERTIFICATE OF CORRECTION

PATENT NO.    : 6,773,631 B2
DATED         : August 10, 2004
INVENTOR(S)   : James E. Reddy et al.

It is certified that error appears in the above-identified patent and that said Letters Patent is hereby corrected as shown below:

Column 11,
Line 1, "Minolta calorimeter" should be -- Minolta colorimeter --

Column 13,
Line 63, "at 90° C." should be -- at 190° C. --

Column 14,
Lines 51-52, "thermal stability as shown by Table VII." should be -- thermal stability as shown by Table VIII. --

Column 16,
Line 30, "<reacting a" should be -- reacting a --, and should begin a subparagraph Signed and Sealed this Nineteenth Day of April, 2005

JON W. DUDAS
*Director of the United States Patent and Trademark Office*